United States Patent
Berting

(10) Patent No.: US 8,275,445 B2
(45) Date of Patent: Sep. 25, 2012

(54) SYSTEM AND METHOD FOR DETERMINING THE POSITION OF AN INSTRUMENT

(75) Inventor: Andreas Berting, Radmühl (DE)

(73) Assignee: Siemens Aktiengesellschaft, München (DE)

( * ) Notice: Subject to any disclaimer, the term of this patent is extended or adjusted under 35 U.S.C. 154(b) by 683 days.

(21) Appl. No.: 12/148,803

(22) Filed: Apr. 22, 2008

(65) Prior Publication Data

US 2008/0275334 A1 Nov. 6, 2008

(30) Foreign Application Priority Data

Apr. 26, 2007 (DE) .................. 10 2007 019 827

(51) Int. Cl.
*A61B 5/05* (2006.01)
(52) U.S. Cl. .................. 600/424; 606/130; 600/426
(58) Field of Classification Search .......... 600/407–410, 600/424–430; 606/130
See application file for complete search history.

(56) References Cited

U.S. PATENT DOCUMENTS

| | | | |
|---|---|---|---|
| 5,255,680 A | 10/1993 | Darrow et al. | |
| 7,344,307 B2 * | 3/2008 | Yatsenko et al. | 378/207 |
| 7,580,503 B2 * | 8/2009 | Nekovar et al. | 378/42 |
| 7,636,595 B2 * | 12/2009 | Marquart et al. | 600/424 |
| 7,671,887 B2 * | 3/2010 | Pescatore et al. | 348/25 |
| 7,835,779 B2 * | 11/2010 | Anderson et al. | 600/407 |
| 7,835,784 B2 * | 11/2010 | Mire et al. | 600/424 |
| 2003/0095638 A1 | 5/2003 | Sabczynski et al. | |
| 2004/0138548 A1 * | 7/2004 | Strommer et al. | 600/407 |
| 2005/0033149 A1 * | 2/2005 | Strommer et al. | 600/407 |
| 2005/0085714 A1 * | 4/2005 | Foley et al. | 600/424 |
| 2006/0115054 A1 * | 6/2006 | Yatsenko et al. | 378/207 |
| 2006/0116571 A1 | 6/2006 | Maschke et al. | |
| 2006/0241372 A1 * | 10/2006 | Nekovar et al. | 600/407 |
| 2008/0097187 A1 * | 4/2008 | Gielen et al. | 600/409 |
| 2008/0101668 A1 * | 5/2008 | Boyden et al. | 382/128 |
| 2008/0195109 A1 * | 8/2008 | Hunter et al. | 606/87 |
| 2010/0234724 A1 * | 9/2010 | Jacobsen et al. | 600/424 |

FOREIGN PATENT DOCUMENTS

| | | |
|---|---|---|
| DE | 10156443 A1 | 5/2003 |
| DE | 102004058008 A1 | 6/2006 |
| DE | 102005014286 A1 | 10/2006 |

\* cited by examiner

*Primary Examiner* — Sanjay Cattungal

(57) ABSTRACT

The invention relates to a system and a method for a system featuring an electromagnetic position detection system and an instrument of which the position is able to be determined in at least one electromagnetic field created with the electromagnetic position detection system, with a device distorting the electromagnetic field being located at least partly in the electromagnetic field or a device distorting the electromagnetic field being able to be brought at least partly into the electromagnetic field, and with the position of the instrument being determined taking into account the position of the device or of a part of the device in the electromagnet field and the distortion of the electromagnetic field associated with it.

14 Claims, 1 Drawing Sheet

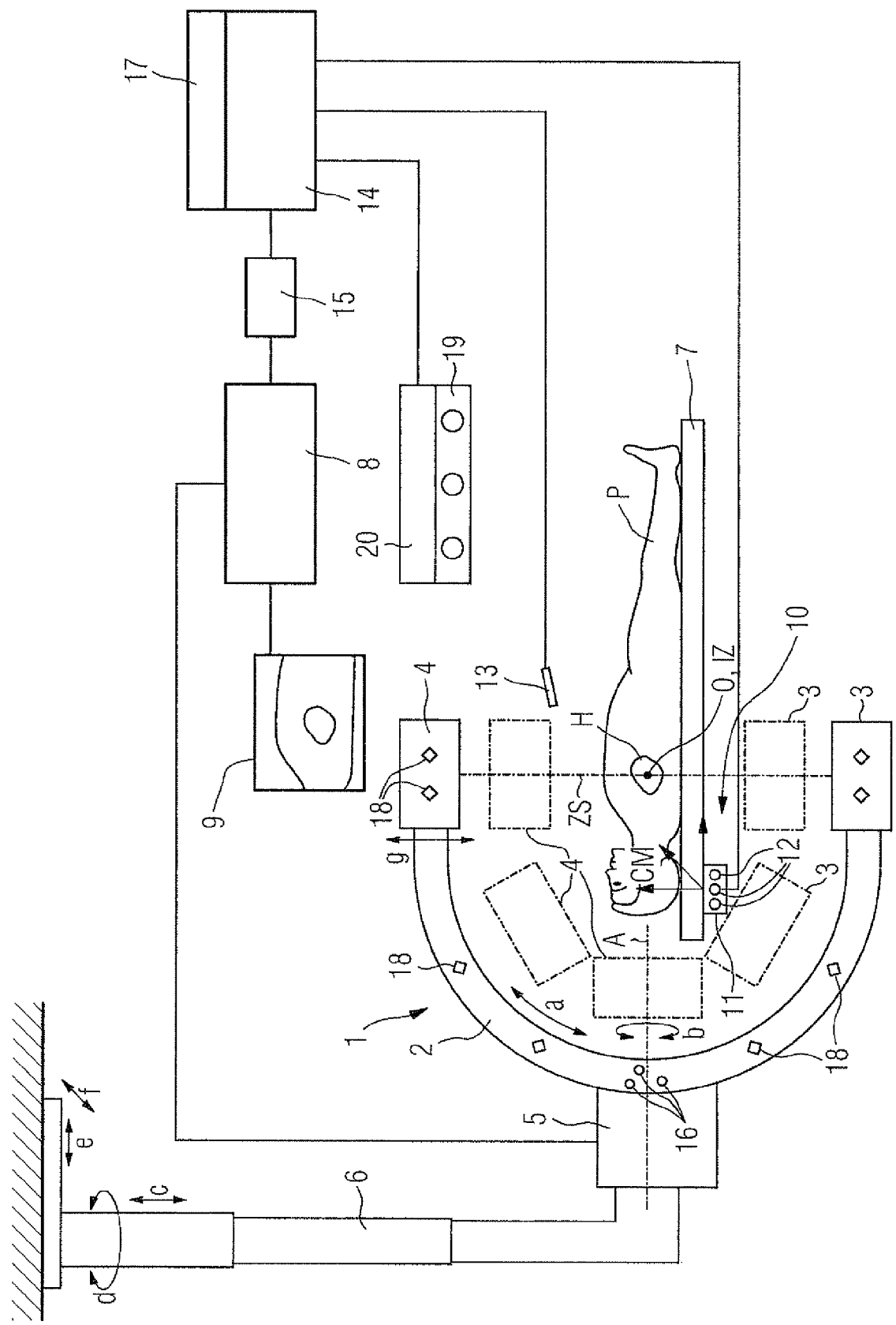

SYSTEM AND METHOD FOR DETERMINING THE POSITION OF AN INSTRUMENT

CROSS REFERENCE TO RELATED APPLICATIONS

This application claims priority of German application No. 10 2007 019 827.4 filed Apr. 26, 2007, which is incorporated by reference herein in its entirety.

FIELD OF THE INVENTION

The invention relates to a system and a method for determining the position of an instrument. The system features an electromagnetic position detection system, an instrument, of which the position is able to be determined in at least one electromagnetic field created with the electromagnetic position detection system, and with a device able to be brought at least partly into the electromagnetic field.

BACKGROUND OF THE INVENTION

This type of system is employed as a combination system in medical engineering for example and, as well as an electromagnetic position detection and mapping system, can feature an angiography system with a C-arm x-ray device. Medical interventions into a patient are supported by the system, with for example the instrument being navigated or guided in the patient on the basis of images of the patient obtained with the C-arm x-ray device and position data obtained with the electromagnetic position detection and mapping system of the instrument, by an image of the instrument being inserted into the images obtained with the C-arm x-ray device. For this purpose the electromagnetic position detection and mapping system and the C-arm x-ray device or the electromagnetic position detection and mapping system and the images obtained with the C-arm x-ray device generally registered with one another, so that an image of the instrument can be edited into the images.

U.S. Pat. No. 5,255,680 A for example describes a device which features an electromagnetic signal tracking system, a medical instrument able to be introduced into the body of a patient and an x-ray device. The medical instrument able to be introduced into the body of a patient comprises a coil for creating an electromagnetic field. Once the medical instrument is introduced into the body of the patient and creates the electromagnetic field, this field is detected by receive coils arranged on the x-ray device, with a tracking/display unit determining the positions of the medical instrument in the body of the patient. Furthermore during of a medical intervention into the patient fluoroscopy images of the patient into which a mark characterizing the positions of the medical instruments in the body of the patient is inserted are recorded at specific intervals.

In this way for example puncturings, general catheter application or catheter applications at the heart of a patient can be supported, in which the instrument, be it a puncturing needle or a catheter, after penetration into the patient can at least partly no longer be followed visually by eye, but must be navigated or guided in the patient with reference to the images.

Thus, in the treatment of heart arrhythmias of a patient by means of ablation an ablation catheter is introduced with the aid of x-ray images obtained with the C-arm x-ray device of the angiography system, be they 2D or 3D images, via veins or arteries into a heart chamber of the patient and the tissue causing the heart arrhythmias is removed by high-frequency current. The prerequisite for successfully carrying out a catheter ablation is on the one hand the precise pinpointing of the cause of the heart arrhythmias in the heart chamber and on the other hand the precise cauterization of the tissue causing the heart arrhythmias. The tissue concerned is pinpointed in an electrophysiological examination, in which the electrical potentials are recorded locally resolved with a mapping catheter introduced into the heart chamber. 3D mapping data of the heart chamber is obtained from this electrophysiological examination, the so-called electroanatomical mapping, for example, which can be visualized on a display device. The mapping function and the ablation function are also frequently combined in one catheter, so that the mapping catheter is simultaneously also an ablation catheter.

A known electroanatomical 3D mapping method, as is able to be performed for example with the CARTO system from Biosense Webster Inc., USA, is based on the electromagnetic principle. Transmitters arranged below a patient generally establish three, but with the systems currently being widely employed, even nine different electromagnetic fields of low intensity. By means of electromagnetic sensors integrated into the catheter tip of the mapping catheter it is then possible to measure the voltage changes within the electromagnetic fields induced by the catheter movements and, with the aid of mathematical algorithms, to compute the position of the mapping catheter at any given point in time. By scanning the contour of a heart chamber point-by-point with the mapping catheter while simultaneously detecting the electrical signals of the sensors, 3D mapping data is obtained or an electroanatomical three-dimensional map is produced in which the electrical signals can be reproduced color-coded.

The most accurate possible determination of the positions of the mapping catheter or of the ablation catheter is of decisive importance in this case for obtaining high-quality mapping data and to enable the mapping catheter or the ablation catheter to be navigated according to the actual anatomy of the patient in the body of the patient with reference to the mapping data and/or to the images obtained with the C-arm x-ray device. Inaccuracies in determining the positioning of the mapping catheter or of the ablation catheter lead in the diagnostics or the therapy, for example in the diagnostics and therapy of stimulus formation and stimulus conduction problems in the heart, to less than optimum results. Not infrequently examinations and interventions taking several hours are able to be traced back in the electrophysiological laboratory to inaccuracies in the position determination of a mapping or ablation catheter.

SUMMARY OF THE INVENTION

The invention is thus based on the object of specifying a system and a method if the type specified at the start of making the determination of the position of the instrument more accurate.

In accordance with the invention this object is achieved by a system and a method for a system featuring an electromagnetic signal position detection system and an instrument, of which the position is determined in at least one electromagnetic field created with the electromagnetic position detection system, with a devices distorting the electromagnetic field being located at least partly in the electromagnetic field or a device distorting the electromagnetic field able to be brought at least partly into the electromagnetic field and with the determination of the position of the instrument taking into account the position of the device or of a part of the device in the electromagnetic field and the influencing or distortion of the electromagnetic field occurring.

The inventor has recognized that the introduction of a device or of a part of a device into an electromagnetic field created by the electromagnetic position detection system can result in a distortion or distortions of the electromagnetic fields, which produces a negative effect on the accuracy of the localization or the accuracy of the determination of the position of the instrument in the electromagnetic field with the electromagnetic position detection system. It is thus proposed, in the determination of the position of an instrument with an electromagnetic position detection system in an electromagnetic field created with the electromagnetic position detection system, to take into account the position of the device or of a part of the device in the electromagnetic field and thus of the distortions of the electromagnetic field associated with the device or with the part of the device. In this way the accuracy in the determination of the position of the instrument can be increased. In the medical environment in particular, this results in improved diagnostics and therapy, especially when using catheters. The position detection system can in this case also be embodied as a mapping system as well.

DE 101 56 443 A1 deals with the distortion of images taken by a magnetic field-sensitive x-ray image amplifier which can be distorted by the effects of external magnetic fields which surround the image amplifier. In this case it is proposed in DE 101 56 443 A1, to improve the imaging, in a plurality of selected positions of the image amplifier, to determine calibration data with which the distortion can be removed from an image recorded in the respective setting of the image amplifier. In the respective settings the respective magnetic field data operating on the image amplifier is determined and assigned to the calibration data. To this end the amplifier features a three-axis magnetometer, with which in operation in each position of the image amplifier the outer magnetic field in the immediate environment of the image amplifier is measured in respect of its direction and its strength. This magnetic field data is stored together with the calibration data in a look-up table.

In accordance with one embodiment of the invention the electromagnetic position detection system features at least one transmitter for creating the at least one electromagnetic field and the instrument features at least one sensor. Preferably the electromagnetic position detection system features at least three transmitters for creating three different electromagnetic fields and the instrument, for example in the tip of the instrument, has at least three sensors for determining the position of the instrument in the three electromagnetic fields of the transmitter.

In accordance with a variant of the invention, the device which is moved at least partly into the at least one electromagnetic field of the electromagnetic position detection system, is a C-arm x-ray device. The C-arm x-ray device can in this case be part of an angiographic system.

In accordance with a further variant of the invention the instrument is a catheter, especially a mapping and/or ablation catheter. The catheter can be a catheter of the electromagnetic position detection system, which has as a rule in the catheter tip three sensors for determining the positioning of the catheter in the electromagnetic fields of the electromagnetic position detection system.

An embodiment of the invention makes provision for at least one position sensor of the electromagnetic position detection system to be arranged in a defined manner on the device or on the part of the device. Preferably three position sensors of the electromagnetic position detection system are arranged in a defined manner on the device or the part the device, so that by detecting the three position sensors, the electromagnetic position detection system can always detect and determine the position of the device or of the part of the device in the electromagnetic fields of the electromagnetic position detection system. This creates the prerequisites that the distortions of the electromagnetic fields which depend on the position of the device or of a part of the device in the electromagnetic fields are able to be taken into account for the determination of the position of the instrument.

In accordance with a variant of the invention a further position detection system is provided for determining the position of the device or of the part of the device. This can involve an optical position detection system or a system based on infrared radiation.

In accordance with another embodiment of the invention the device and the electromagnetic position detection system are connected to each other via at least one interface for transmission of position data of the device or of parts of the device to the electromagnetic position detection system. If the electromagnetic position detection system and the device are arranged in a defined manner relative to each other, which means that in relation to at least one defined initial position, the position of the device and/or of parts of the device is known in relation to the electromagnetic position detection system, if there is a change in the position of the device or a part of the device relative to the electromagnetic position detection system, the changed position data of the device can be transmitted to the electromagnetic position detection system via the interface, so that the current position data of device or of a part of the device are always known to the electromagnetic position detection system. The positions can be specified in such cases with reference to a coordinate system assigned to the electromagnetic position detection system.

In accordance with a variant of the invention the distortions of the electromagnetic fields are determined analytically and/or numerically by field computation based on the position of the device or of a part of the device in the electromagnetic field and on the material or the materials from which the device or a part the device is embodied, and/or on the dimensions of the device or of a part of the device. Starting from the known electromagnetic field or the known electromagnetic fields of the electromagnetic position detection system, the field distortions produced by the device or a part of the device of the electromagnetic fields of the electromagnetic position detection system can thus be determined and taken into account accordingly in the determination of the position of the instrument. The field computations can be undertaken online in such cases by a computing device of the electromagnetic position detection system. Commercially-available field computation programs, for example "ANSYS" from CADFEM, can be used for this purpose.

In accordance with another embodiment of the invention a calibration of the system is undertaken to take account of the distortions of the electromagnetic fields caused by the device or a part of the device. Calibration data is recorded and stored during the calibration, to enable said data to be used subsequently in the determination of the position of the instrument.

The calibration is preferably undertaken such that the device or a part of the device and the instrument assume different defined positions relative to each other in the electromagnetic field and in each case at least one item of calibration data for example in the form of the resulting displacement in each case, is determined in the position determination of the instrument, by the position of the instrument being determined with and without the presence of the device or of the part of the device in the electromagnetic field. In this way, for different defined constellations of the device or a part of the device and of the instrument relative to one another at least one item of calibration data or a correction value for the position determination unit of the instrument is obtained, which can be included in the productive use of the system for the actual position determination of the instrument. If a constellation in the productive use of the system thus matches a calibration constellation, based on the correction value determined for this, the position of the instrument in the electromagnetic field of the electromagnetic position detection system can be determined.

Since an item of calibration data cannot be determined for each constellation, a variant of the invention makes provision that, for determining the position of the instrument in the electromagnetic field in the presence of the device or of a part of the device in the electromagnetic field, an interpolation is undertaken based on calibration data determined. In the simplest case the positions of the device or of a part of the device and of the instrument in the electromagnetic field are determined and, should no calibration or correction value have been detected for these positions of the device or of a part of the device and of the instrument, the correction value needed is determined from two correction values which are assigned to adjacent positions of the device or of the part of the device and of the instrument.

BRIEF DESCRIPTION OF THE DRAWINGS

Exemplary embodiments of the invention are presented in the enclosed schematic drawing which shows an inventive system for carrying out the inventive method.

DETAILED DESCRIPTION OF THE INVENTION

In the case of the present exemplary embodiment the system comprises a device in the form of a C-arm x-ray device 1, which is part of an angiography system not shown in any greater detail. The C-arm x-ray device 1 features a C-arm 2 on which, opposite one another, an x-ray source 3 featuring a collimator and an x-ray detector 4 are arranged. A central ray ZS of an x-ray bundle emitted by the x-ray source 3 passes in the case of the present exemplary embodiment at least essentially through the isocenter IZ of the C-arm 2 and hits at least approximately centrally the entry window of the x-ray detector 4. The C-arm 2 is supported to allow adjustments on a mount 5 around its orbital axis 0 in the directions of the double arrow. In the case of the present exemplary embodiment the mount 5 is arranged on a ceiling stand 6, which provides the adjustment options indicated in the figure by double arrows c, d, e and for the mount 5 provided with the C-arm 2. In addition the mount 5 with the C-arm 2 is able to be swiveled around the axis of angulation A in the directions of the double arrow b. In addition the distance between the x-ray source 3 and the x-ray detector 4 (focus detector distance) can vary, which is indicated by double arrow g.

The C-arm x-ray device 1 features a plurality of position generators not shown in the diagram, by which changes in the position of components of the C-arm x-ray device 1 are detected, with a current position of a component of the C-arm x-ray device 1 being available in each case in the computer 8 of the C-arm x-ray device 1. If for example the C-arm 2 is adjusted around its orbital axis 0 in a direction of the double arrow a, this movement is detected by the position generator and the current positions of the C-arm 2 as well as the x-ray source 3 arranged in a defined position on the C-arm 2 and of the x-ray detector 4 arranged in a defined position on the C-arm 2 are available in the computer 8 of the C-arm x-ray device 1. The behavior is the same for adjustments of the mount 5 by means of the ceiling stand 6.

2D x-ray image and 3D images of an object can be obtained in the known way with the C-arm x-ray device 1. In the case of the present exemplary embodiment the object is a patient P supported on a schematically depicted patient table 7. As a rule the patient table 7 with the patient P and the C-arm 2 of the C-arm x-ray device are aligned relative to one another such that an area of tissue of the patient P of interest to be imaged in an x-ray image at least essentially ends up in the isocenter IZ of the C-arm 2. Otherwise the C-arm x-ray device 1 and the patient table 7 are aligned relative to one another and registered in a defined manner in relation to each other, i.e. changes of position of the patient table 7 are also for example detected via position generators and are available to the computer 8.

In addition to the C-arm x-ray device 1, in the case of the present exemplary embodiment, an electromagnetic position detection and mapping system 10 is available as an electromagnetic position detection system. The electromagnetic position detection and mapping system 10 features in the case of the present exemplary embodiment, a transmitter unit 11 with three transmitters 12, an ablation and mapping catheter 13 as well as a processing unit 14. The transmitter unit 11 and the ablation and mapping catheter 13 are connected to the computation unit 14 which is operated by an operating program for the electromagnetic position detection and mapping system 10. In the case of the present exemplary embodiment the transmitter unit 11 is arranged in a defined manner on the patient table 7 which, as already mentioned, is registered with the C-arm x-ray device.

The transmitters 12 of the transmitter unit 11 each create a defined electromagnetic field, with the three electromagnetic fields created by the transmitters 12 differing from one another. Three sensors are provided in the tip of the ablation and mapping catheter 13 in a manner not shown in any greater detail in the figure. If the ablation and mapping catheter 13 is moved in the electromagnetic alternating fields of the transmitter 12, the position of the ablation and mapping catheter 13 can be determined with the computing device 14 of the electromagnetic position detection and mapping system 10 in a coordinate system CM assigned to the electromagnetic position detection and mapping system 10. In this case the voltage changes induced within the electromagnetic fields of the transmitter 12 by the movements of the ablation and mapping catheter 13 are measured with the electromagnetic sensors integrated into the tip of the ablation and mapping catheter 13 and the position of the ablation and mapping catheter 13 is determined at any given point in time with the aid of mathematical algorithms.

This is of especial significance if the ablation and mapping catheter 13 is introduced for diagnostic or therapeutic purposes into the body of the patient P and can no longer be followed visually by eye. By determining the position of the oblation and mapping catheter 13 in the patient P an image of the ablation and mapping catheter 13 can be inserted for example into a 3D image which can be displayed on a display unit can be obtained with the C-arm x-ray device 1. This is possible if the C-arm x-ray device 1 and the electromagnetic position detection system and mapping system 10 are registered relative to one another, which is the case here. To edit an image of the oblation and mapping catheter 13 into an image obtained with the C-arm x-ray device 1 it is however also simply sufficient to register the respective image and the electromagnetic position detection and mapping system 10 relative to one another.

Furthermore mapping data, for example 3D mapping data, can be obtained with the ablation and mapping catheter 13 during an application of a catheter to the heart H of the patient P. By scanning areas of a heart chamber point-by-point with the ablation and mapping catheter 13 with simultaneous detection of the electrical signals of the sensors, a three-dimensional electroanatomical map is produced or 3D mapping data is generated, with the electrical signals being able to be reproduced by color codes for example.

In the detection of the positions of the ablation and mapping catheter 13, be it for navigation of the ablation and mapping catheter 13 or for obtaining 3D mapping data, it frequently occurs that at least parts of the C-arm x-ray device 1 such as the C-arm 2, the x-ray source 3 or the x-ray detector 4, are introduced into the electromagnetic fields of the electromagnetic position detection and mapping system 10 created by the transmitters 12 or are located in the electromagnetic fields, especially if the ablation and mapping catheter 13 is navigated using facilities such as x-ray images in the body of the patient P. The components of the C-arm x-ray device 1 introduced into the electromagnetic fields of the electromagnetic position detection and mapping system 10 influence in such cases the electromagnetic fields and give rise to distortions, which has a negative effect on the accuracy of the determination of the positions of the ablation and mapping catheter 13 and thus also on the incorporation of an image of the ablation and mapping captor 13 into an image obtained with the C-arm x-ray device 1 or on obtaining mapping data. These inaccuracies in the position determination lead especially to a less than optimum therapy for catheter applications in the heart, for example in the therapy of stimulus creation and stimulus conduction problems in the heart. In addition this makes the duration of the investigations and interventions longer.

It is thus proposed that the position of the ablation and mapping catheter 13 be determined taking into consideration the position of the C-arm x-ray device 1 or at least one component of the C-arm x-ray device 1, such as the x-ray detector 4 or the x-ray source 3, the collimator of which causes the highest relative field distortion in the electromagnetic fields and the associated distortions of the electromagnetic fields.

In accordance with an embodiment of the invention, starting from the known electromagnetic fields created by the transmitters 12, the distortions of the electromagnetic fields can be determined analytically and/or numerically by field computations with the computation device 14 of the electromagnetic position detection and mapping system 10. The field computations are undertaken on the basis of the current position and in the knowledge of the materials and the dimensions of the C-arm x-ray device 1 or at least one component of the C-arm x-ray device 1.

For the present exemplary embodiment it is assumed that at least a part of the C-arm 2 and of the x-ray detector 4 are located in the electromagnetic fields created by the transmitters 12. To enable the corresponding field computations to be undertaken with the computation device 14 for the three electromagnetic fields of the transmitters 12, the positions of the C-arm 2 and of the x-ray detector 4 in the electromagnetic fields are required.

The C-arm x-ray device 1 and the patient table 7, on which the transmitters 12 are arranged in a defined manner, are arranged in a defined manner in relation to one another. This means that the positions of the C-arm x-ray device 1 in a coordinate system CM assigned to the electromagnetic position detection and mapping system 10 are known. A change of the position of the C-arm x-ray device 1 or a component of the C-arm-x-ray device 1, such as the C-arm 2 or the x-ray detector 4, is detected by the position generator mentioned and transmitted to the computer 8, so that the current positions, especially of the C-arm 2 and also of the x-ray detector 4, are available in the computer 8. Likewise the dimensions of the C-arm 2 and of the x-ray detector 4, as well as the materials from which the C-arm 2 and the x-ray detector 4 are made, are known and available to the computing device 14. The current positions of the C-arm 2 and of the x-ray detector 4 are available to the computing device 14 via an interface 15. Alternatively position sensors 16 of the electromagnetic position detection system and mapping system 10, for example on the C-arm 2, can be arranged in a defined manner in order to be able to determine themselves with the aid of the electromagnetic position detection and mapping system 10 the positions of the C-arm 2 and of the x-ray detector 4 arranged in a defined manner on the C-arm.

Furthermore there is the option of determining the positions of the C-arm 2 and the components arranged on it with another position detection system, for example an optical position detection system or a system based on infrared radiation. To this end optical markers 18 and/or reflectors can be arranged on the C-arm 2 and/or the x-ray source 3 and/or the x-ray detector 4 which are able to be recorded by a camera system 19, so that the positions are able to be determined with a computing device 20 of the optical position detection system and by the computing device 14.

Based on the position, material and dimension information, online field computations for the three electromagnetic fields created by the transmitters can be undertaken by the computing device 14 with an appropriate program, especially in respect of their changes or distortions by the introduction of a part of the C-arm 2 and of the x-ray detector 4 into the originally created electromagnetic fields.

If the distortions of the electromagnetic fields by the C-arm 2 and the x-ray detector 4 are defined, these can be taken into consideration by the computing device 14 in the actual determination of the position of the ablation and mapping catheter 13 with the electromagnetic position detection and mapping system 10 and the positions of the ablation and mapping catheter 13 able to be determined with greater accuracy with the electromagnetic position detection and mapping system 10.

In accordance with a second embodiment of the invention the distortions of the electromagnetic fields of the transmitters 12 caused by a part of the C-arm 2 and/or the x-ray source 3 and/or the x-ray detector 4 are taken into account by a calibration of the system. The calibration of the system, i.e. of the C-arm x-ray device 1 and of the electromagnetic position detection system and mapping system 10 relative to one another is undertaken such that the C-arm x-ray device 1, especially components of the C-arm x-ray device 1 and of the ablation and mapping catheter 13, assume different defined positions relative to one another in the created electromagnetic fields of the transmitters 12. The ablation and mapping catheter 13 can be arranged for this on a stand not shown in the figure which is able to change its position, to enable defined reproducible positions to be assumed.

For each constellation of the C-arm x-ray device 1 and of the ablation and mapping catheter 13 assumed relative to one another, the position of the ablation and mapping catheter 13 is determined once without the presence of the C-arm x-ray device 1 and once with the presence of the C-arm x-ray device 1 in the electromagnetic fields of the transmitters 12 and, on the basis of this position data, at least one item of calibration data in each case in the form of the respective resulting displacement is determined in the position determination unit of the ablation and mapping catheter in which a correction value is involved. The calibration or correction value determined for the respective constellation is preferably stored in a memory 17 of the computing device 14, so that this value is available for subsequent position determination of the ablation and mapping catheter 13.

Different positions of the x-ray detector 4 and the x-ray source 3 relative to the ablation and mapping catheter 13 are indicated as examples in the figure, which each illustrate a constellation and for which a correction value is determined in each case. Preferably correction values or calibration values respectively are determined for those positions of the C-arm x-ray device 1, especially of the C-arm 2 equipped with the x-ray source 3 and the x-ray detector 4, which are frequently assumed for a catheter application in the heart. Thus for example correction values for the C-arm 2 can be determined if this has a cranial, caudal, LAO (left anterior orientation) or RAO (right anterior orientation) disposition. Furthermore correction values can be determined for different x-ray source—x-ray detector distances or detector focus distances. In this case the ablation and mapping catheter 13 also assumes different respective positions. In this way a plurality of calibration data in the form of correction values is obtained for the most precise determination possible of the position of the ablation and mapping catheter 13 with the electromagnetic position detection and mapping system 10. Since correction values cannot be determined for all constellations of the C-arm x-ray device 1 and the ablation and mapping catheter 13 relative to each other, the computing device 14 is configured in programming terms so that to determine a position of the ablation and mapping catheter 13 in the electromagnetic fields of the transmitters 12 in the presence of the C-arm x-ray device 1 or of a component of the C-arm x-ray device 1 in the electromagnetic fields, an interpolation of a correction value based on calibration data and correction values determined and stored can be undertaken. In the simplest version in this case interpolation is undertaken between two correction values to enable the position of the ablation and mapping catheter 13 to be determined as accurately as possible.

In the case of the present exemplary embodiment, when the system is used based on the determined positions of the C-arm 2 and of the x-ray detector 4 as well as of the ablation and mapping catheter 13, the respective calibration or correction value is taken from the memory 17 and the position of the ablation and mapping catheter 13 is defined as precisely as possible with the calibration or correction value obtained.

The taking into account described of the distortions caused by the C-arm x-ray device 1 or by components of the C-arm x-ray device 1 of the electromagnetic fields of the transmitters 12 markedly increases the accuracy in the determination of the position of the ablation and mapping catheter 13, which has the effect of improving diagnostics and therapy, especially for catheter applications in the heart of the patients, so that examinations lasting several hours and interventions in the electrophysiological laboratory can often be very much shortened.

The instrument involved also does not absolutely have to be a catheter. Instead the instrument can also be a puncturing needle, a probe or another facility introduced into the body of a patient.

Likewise the device does not necessarily have to be a C-arm x-ray device. For example the device can be another imaging device such as a computer tomography device or an ultrasound device.

The invention has been explained above using a medical system as an example. The invention is however not restricted to a medical system or to the field of medicine.

The invention claimed is:

1. A system for determining a position of an instrument in a procedure, comprising:
   an electromagnetic position detection system comprising a transmitter that creates an electromagnetic field;
   an x-ray device having a C-arm, an x-ray source, and an x-ray detector that distorts the electromagnetic field;
   a position sensor of the electromagnetic position detection system arranged on the C-arm that determines a position of the x-ray device in the electromagnetic field; and
   a further position detection system for determining positions of the C-arm, the x-ray source, and the x-ray detector, wherein the further position detection system comprises:
   optical markers arranged on the C-arm, the x-ray source, and the x-ray detector, and
   a camera that records the positions of the optical markers,
   wherein the electromagnetic position detection system is configured to determine the position of the instrument based on the position of the x-ray device in the electromagnetic field and the distortion of the electromagnetic field.

2. The system as claimed in claim 1, wherein the instrument comprises a sensor.

3. The system as claimed in claim 1, wherein the instrument is a catheter.

4. The system as claimed in claim 1, wherein the x-ray device and the electromagnetic position detection system are linked to each other via an interface for transmitting data of the position of the x-ray device to the electromagnetic position detection system.

5. The system as claimed in claim 1, wherein the distortion of the electromagnetic field is determined analytically or numerically by a field calculation based on the position of the x-ray device, material of the device, or dimensions of the x-ray device.

6. The system as claimed in claim 1, wherein the instrument is located at least partly in the electromagnetic field or able to be brought at least partly into the electromagnetic field.

7. The system as claimed in claim 1, wherein the positions of the C-arm, the x-ray source, and the x-ray detector are used in determining the position of the instrument.

8. The system as claimed in claim 1, wherein the electromagnetic position detection system and the x-ray device are calibrated for the distortion of the electromagnetic field.

9. The system as claimed in claim 8, wherein resulting displacements are determined for the calibration.

10. The system as claimed in claim 8, wherein data of the calibration is interpolated for determining the position of the instrument.

11. A method for determining a position of an instrument in a procedure, comprising:
    creating an electromagnetic field by an electromagnetic position detection system comprising a transmitter;
    distorting the electromagnetic field by an x-ray device having a C-arm, an x-ray source, and an x-ray detector;
    determining a position of the x-ray device in the electromagnetic field by a position sensor of the electromagnetic position detection system arranged on the C-arm;
    determining the position of the instrument based on the position of the x-ray device in the electromagnetic field and the distortion of the electromagnetic field; and determining positions of the C-arm, the x-ray source, and the x-ray detector by a further position detection system, wherein the further position detection system comprises:
   optical markers arranged on the C-arm, the x-ray source, and the x-ray detector, and
   a camera that records the positions of the optical markers.

12. The method as claimed in claim 11, wherein the instrument is a catheter.

13. The method as claimed in claim 11, wherein the instrument is located at least partly in the electromagnetic field or able to be brought at least partly into the electromagnetic field.

14. The method as claimed in claim 11, wherein a position of a part of the x-ray device is used in determining the position of the instrument.

* * * * *